(12) United States Patent
Liu et al.

(10) Patent No.: US 11,788,110 B2
(45) Date of Patent: Oct. 17, 2023

(54) METHOD FOR ENZYMATIC PREPARATION OF GLUTATHIONE

(71) Applicant: ANHUI GSH BIO-TECH CO., LTD, Anhui (CN)

(72) Inventors: Shanshan Liu, Beijing (CN); Hui Liu, Beijing (CN); Wenwen Zhou, Beijing (CN); Yongfa Qin, Beijing (CN)

(73) Assignee: ANHUI GSH BIO-TECH CO., LTD., Anhui (CN)

( * ) Notice: Subject to any disclaimer, the term of this patent is extended or adjusted under 35 U.S.C. 154(b) by 528 days.

(21) Appl. No.: 16/622,856

(22) PCT Filed: Jun. 6, 2018

(86) PCT No.: PCT/CN2018/090045
§ 371 (c)(1),
(2) Date: Dec. 13, 2019

(87) PCT Pub. No.: WO2018/228246
PCT Pub. Date: Dec. 20, 2018

(65) Prior Publication Data
US 2020/0199641 A1    Jun. 25, 2020

(30) Foreign Application Priority Data
Jun. 15, 2017 (CN) .......................... 201710452240.9

(51) Int. Cl.
*C12P 21/02* (2006.01)
*C07K 1/30* (2006.01)

(52) U.S. Cl.
CPC .............. *C12P 21/02* (2013.01); *C07K 1/306* (2013.01)

(58) Field of Classification Search
CPC ................................ C12P 21/02; C07K 1/306
See application file for complete search history.

(56) References Cited

FOREIGN PATENT DOCUMENTS

| CN | 105219823 | A | * | 1/2016 | |
|---|---|---|---|---|---|
| CN | 105603028 | A | * | 5/2016 | |
| CN | 106191170 | A | * | 12/2016 | ............... C12P 19/32 |
| CN | 106220708 | A | * | 12/2016 | ............ C07K 5/0215 |
| CN | 105603028 | B | * | 4/2019 | |

OTHER PUBLICATIONS

CN-105219823-A. Translation of Liu, "Method for preparing glutathione by means of enzymic method". Retrieved from Espacenet. (Year: 2016).*
CN-106191170-A. Translation of Liu, "Method for preparing triphosadenine by enzymic method". Retrieved from Espacenet. (Year: 2016).*
CN-106220708-A. Translation of Liu, "Method for extracting and separating glutathione from GSCu precipitate". Retrieved from Espacenet. (Year: 2016).*
CN-105603028-A. Translation of Huang, "Enzymic method for simultaneously preparing glutathione and adenylate". Retrieved from Espacenet. (Year: 2016).*
Leider, "The Invisible Companion in Biomaterials Research". Tissue Engineering: Part B; vol. 19, No. 5, 2013. Retrieved <URL: https://www.liebertpub.com/doi/10.1089/ten.teb.2012.0636> (Year: 2013).*
ARL Bio Pharma, "The Importance of Endotoxin Testing". Retrieved <URL: https://www.arlok.com/news/the-importance-of-endotoxin-testing> (Year: 2012).*
CN-105603028-B Translation of Liu, "Enzymic method for simultaneously preparing glutathione and adenylate". Retrieved from Espacenet. (Year: 2016).*
Chandler, "Regional Creatine Kinase, Adenylate Kinase, and Lactate Dehydrogenase in Normal Canine Brain". Stroke; vol. 19, No. 2, 1988. Retrieved <URL: https://www.ahajournals.org/doi/pdf/10.1161/01.STR.19.2.251> (Year: 1988).*
Ichige, "Inorganic polyphosphate kinase and adenylate kinase participate in the polyphosphate:AMP phosphotransferase activity of *Escherichia coli*". Proc Natl Acad Sci USA, 19;97(26):14168-71, 2000. Retrieved <URL: https://www.ncbi.nlm.nih.gov/pmc/articles/PMC18889/pdf/pq014168.pdf> (Year: 2000).*

* cited by examiner

*Primary Examiner* — Robert J Yamasaki
(74) *Attorney, Agent, or Firm* — BOOTH UDALL FULLER, PLC; Pacer K. Udall (57) ABSTRACT

The present invention relates an enzymatic method for preparing glutathione, comprising the following steps: (1) producing glutathione in a reactor using GshF enzyme, ATP regeneration enzyme and AK enzyme; (2) separating immobilized GshF enzyme, ATP regeneration enzyme and AK enzyme in the reactor, or separating free GshF enzyme using a filtration device; (3) separating the filtrate obtained in step (2) to obtain a crude product GSH and a small amount of ATP, ADP and AMP; and (4) subjecting the GSH obtained in step (3) to concentration, crystallization, and drying to prepare a finished GSH. The described method provides: greatly reduced industrial production costs; faster reaction rate; stable enzyme recovery system that is energy efficient and environmentally friendly; and capability of reusing the byproducts or collecting them for the production of ATP.

13 Claims, 2 Drawing Sheets

METHOD FOR ENZYMATIC PREPARATION OF GLUTATHIONE

CROSS REFERENCE TO RELATED APPLICATIONS

This application is the U.S. National Stage of International Application No. PCT/CN2018/090045, filed Jun. 6, 2018, which claims the benefit of Chinese Patent Application No. CN201710452240.9, filed Jun. 15, 2017, the contents of each of which are incorporated herein by reference in their entireties.

TECHNICAL FIELD

The present invention relates to a method for preparing glutathione, in particular to an enzymatic method for preparing glutathione, specifically to an enzymatic method for preparing glutathione using adenosine instead of adenosine triphosphate (ATP).

BACKGROUND ART

Glutathione is widely found in animals, plants and microorganisms, and is one of the most important non-protein thiol-containing compounds in organisms. Glutathione exists in two types: reduced glutathione (GSH) and oxidized glutathione (GSSG). GSH is abundant in organisms and plays a major role. It is widely used for the treatment of liver diseases, tumors, oxygen poisoning, aging and endocrine diseases, and is used as a bioactive additive and antioxidant in the fields of food and cosmetics.

GSH is a tripeptide formed of glutamic acid (Glu), cysteine (Cys) and glycine (Gly) via 2 peptide bonds. The relative molecular weight is 307.32, and the isoelectric point is 5.93. GSH is a white crystal at room temperature, and is soluble in solvents such as water and aqueous ethanol solution at a low concentration, liquid ammonia and dimethylformamide, etc.

At present, the main preparation methods of glutathione include: solvent extraction method, chemical synthesis method, fermentation method and enzymatic method. As to the extraction method, GSH is extracted from the cereal germs, and this method has been less used because of its low yield of GSH, high cost, serious contamination caused by organic solvents, poor purity, and high consumption of food. The chemical synthesis method is difficult to be popularized since chiral products are not easy to be separated, and the purity of the product is poor. At present, the GSH production adopts the fermentation method world wide. The principle is to clone the gene encoding the GSH synthetase system into bacteria or yeast, and use the microbial fermentation to produce GSH. The fermentation method, especially the yeast fermentation method, is relatively mature in technology, but the batch time is long, the yield is low, and excessive by-products make the downstream processing complicated, and usually, a copper salt method is needed to precipitate GSH, which causes great environmental pollution.

In recent years, the production of GSH by an enzymatic method has been greatly improved. The novel bifunctional glutathione synthetase (GshF, EC 6.3.2.-) has gradually replaced both the original γ-glutamylcysteine synthetase (Gsh I, EC 6.3.2.2) and glutathione synthetase (Gsh II, EC 6.3.2.2) to enzymatically catalyze the production of GSH, which has weak feedback inhibition, and is very suitable for large-scale production.

In theory, whether using a combination of Gsh I and Gsh II enzymes or using a single GshF enzyme to synthesize GSH requires adenosine triphosphate (ATP) as an energy donor. The difficulty in industrial production of GSH at this stage is how to improve the utilization coefficient of ATP to reduce the usage amount of ATP. Generally, at least 3-5 kg of ATP is required to produce 1 kg of GSH, and the cost is high. The patent CN201210201691.2 used yeast glycolysis to regenerate ATP, which had a stable effect. However, the use of yeast will introduce impurities such as pigments in the reaction system to make the further purification difficult. The patents CN201510762184.X and CN201610167664.6 used an enzymatic method to regenerate ATP, which achieved a good effect. ATP regeneration enzyme includes polyphosphate kinase (PPK, EC 2.7.4.1), adenylate kinase (ADK, EC 2.7.4.3), and polyphosphate: AMP phosphotransferase (PAP, EC 2.7.4.-). Among them, PPK enzyme catalyzes the reaction of ADP with polyphosphoric acid or its salt to form ATP, ADK enzyme catalyzes the production of one molecule of ATP and one molecule of AMP by two molecules of ADP, and PAP enzyme catalyzes the reaction of AMP with polyphosphoric acid or its salt to form ADP. ATP can be regenerated by a reasonable combination of the three enzymes of PPK, ADK and PAP. However, the use of this method still requires the addition of a certain amount of ATP for enzymatic reaction.

SUMMARY OF THE INVENTION

The present invention provides an enzymatic method for preparing glutathione, mainly including an enzymatic reaction method of glutathione and a subsequent purification method thereof.

The technical problem to be solved by the present invention is achieved by the following technical solutions:

an enzymatic method for preparing glutathione includes the following steps:

(1) producing glutathione in a reaction tank using GshF enzyme, ATP regeneration enzyme and adenosine kinase (AK) enzyme;

obtaining the GshF enzyme, ATP regeneration enzyme and AK enzyme by genetic engineering, fermentation, and purification, or obtaining the GshF enzyme, ATP regeneration enzyme and AK enzyme by other methods such as natural extraction, wherein, all of the above enzymes may be prepared as an enzyme solution in the form of a free enzyme; or may be further immobilized on an immobilization carrier to obtain an immobilized enzyme, and all of the above enzymes are crude enzyme solutions; and adding the GshF enzyme, ATP regeneration enzyme and AK enzyme in proportion to the reaction system to produce GSH, wherein the reaction system is an aqueous solution containing one or two of a substrate of glutamic acid (Glu) or a salt thereof, cysteine (Cys) or a salt thereof, glycine (Gly) or a salt thereof, adenosine, polyphosphoric acid or a salt thereof, magnesium ions and manganese ions.

In addition, the reaction system may further include one or more of potassium ions, sodium ions, ammonium ions, and one or more of Tris and phosphate ions.

The above substrates, enzymes and various salts may be added to the reaction system in one portion, or may be added in batches according to the industrial production process.

(2) directly separating the immobilized GshF enzyme, ATP regeneration enzyme and AK enzyme, or separating the free GshF enzyme using a filtration device:

directly separating the immobilized GshF enzyme, ATP regeneration enzyme and AK enzyme in the reaction tank/ column, wherein the above separation can be carried out by a filter bag or directly in a reaction column; and the free GshF enzyme, ATP regeneration enzyme and AK enzyme are separated by an ultrafiltration membrane in a filter. Wherein, the filter has a feed port, a discharge port and a reflux port, and an ultrafiltration membrane with a molecular weight cut-off of not more than 20 kDa disposed therein. The retentate after filtration is the recovered enzyme solution, and the filtrate is the reaction solution containing the product without enzyme.

(3) separating the filtrate obtained in step (2) by an ion exchange method to obtain a crude product GSH and a small amount of ATP, ADP and AMP:

adjusting the pH of the filtrate from the previous step to be acidic, and adsorbing and stepwise eluting GSH through a cation exchange resin containing a carboxyl group or a sulfonic group (commercially available) to achieve the purpose of separating GSH and other impurities, wherein the through-liquid from this step mainly contains ATP, ADP and AMP. The substance used for eluting GSH is a combination of one or more of sodium chloride, potassium chloride, ammonium chloride, sodium acetate, ammonium acetate, potassium acetate, hydrochloric acid, and acetic acid.

The separated ATP, ADP and AMP in the through-liquid can be directly added to the reaction system or further separated and purified to obtain a pure product.

(4) concentrating the fraction containing the GSH in the eluate from the previous step by nanofiltration concentration and/or vacuum concentration.

The sodium hydroxide, or potassium hydroxide, or aqueous ammonia is slowly added to the concentrate from the previous step, the pH is adjusted to a range of 5.8 to 7.5, so that GSH can form a solution of sodium salt, potassium salt or ammonium salt at a high concentration; or the concentrate from the previous step can be passed through an H-type cation exchange resin containing an aminophosphonate or a sulfonic group (commercially available) to convert GSH to the H form, and the through-liquid is collected.

Ethanol is added to crystallize GSH during the temperature and stirring speed are controlled. The crystals are collected by filtration and washed with ethanol. The product is obtained by vacuum drying under reduced pressure. Alternatively, GSH can be made into a finished product by spray drying. Alternatively, GSH can be made into a finished product by lyophilization.

Preferably, in the above technical solution, the enzymatic method for preparing glutathione further includes the following steps:

(5) recycling the GshF enzyme, the ATP regeneration enzyme and the AK enzyme separated in step (2): that is, adding the separated GshF enzyme, the ATP regeneration enzyme and the AK enzyme into a reaction tank for a continuous reaction of generating GSH;

(6) continuously separating the GshF enzyme, the ATP regeneration enzyme and the AK enzyme: that is, continuously separating the immobilized GshF enzyme, ATP regeneration enzyme and AK enzyme or continuously separating the free GshF enzyme, ATP regeneration enzyme and AK enzyme using a filtration device.

Preferably, in the above technical solution, step (4) further includes: removing endotoxin using activated charcoal, the activated charcoal being used at a concentration of 0.01-0.5%.

Preferably, in the above technical solution, steps (1) to (6) may be repeated at least once; preferably repeated for a plurality of times, for example, repeated for 2, 3, 4, 5, 6, 7, 8, 9, 10, 15, 20, 25, 30, 40, and 50 times.

Preferably, in the above technical solution, the reaction conditions for producing glutathione in the reaction tank in step (1) are as follows:

the reaction temperature is 25-55° C., preferably the temperature is 30-50° C.;

the reaction pH is 5-10, preferably the pH is 6-9;

the reaction system is a substrate containing a combination of one or more of amino acid or a salt thereof; adenosine; polyphosphoric acid or a salt thereof; magnesium ions or manganese ions; and GshF enzyme, ATP regeneration enzyme and AK enzyme are added to the reaction system to react, so that glutathione is produced.

Preferably, in the above technical solution, the reaction system for generating glutathione in the reaction tank in step (1) further includes: a combination of one or more of sodium ions, potassium ions or ammonium ions; a combination of one or two of Tris or aqueous solution of phosphate, wherein a concentration of potassium ion is 0.01-0.5 M; a concentration of sodium ion is 0.01-0.5 M; a concentration of ammonium ion is 0.01-0.3 M; a concentration of Tris is 0.01-0.1 M; and a concentration of phosphate is 0.01-0.1 M.

Preferably, in the above technical solution, the amino acid or a salt thereof is an L-amino acid or a salt thereof, preferably glutamic acid or a salt thereof (Glu), cysteine or a salt thereof (Cys), and glycine or a salt thereof (Gly). According to its economic cost and optimal reaction conditions, the addition mass ratio of the three amino acids is preferably as follows: Glu:Cys:Gly=(1-2.5):1:(0.5-1.5), more preferably as follows: Glu:Cys:Gly=(1.2-2):1:(0.8-1.5); and the addition concentration of cysteine (Cys) is preferably 1-50 g/L.

Preferably, in the above technical solution, the concentration of adenosine is 0.01-20 g/L, preferably 0.01-5 g/L; the concentration of polyphosphoric acid or a salt thereof is 0.01-0.3 M; and the concentration of magnesium ion is 0.01-0.2 M; and the concentration of manganese ion is 0.005-0.15 M.

Preferably, in the above technical solution, the magnesium ion is selected from the group consisting of one or more of magnesium chloride, magnesium sulfate, magnesium sulfite and magnesium nitrate; and the manganese ion is selected from the group consisting of one or more of manganese chloride and manganese sulfate; the potassium ion is selected from the group consisting of one or more of potassium chloride, potassium sulfate, potassium nitrate, potassium hydroxide, potassium sulfite, potassium carbonate, potassium bicarbonate, potassium acetate, dipotassium hydrogen phosphate, potassium dihydrogen phosphate, and potassium citrate; the sodium ion is selected from the group consisting of one or more of sodium chloride, sodium sulfate, sodium nitrate, sodium hydroxide, sodium sulfite, sodium carbonate, sodium bicarbonate, sodium acetate, disodium hydrogen phosphate, sodium dihydrogen phosphate, and sodium citrate; the ammonium ion is selected from the group consisting of one or more of ammonium chloride, ammonium sulfate, ammonium nitrate, aqueous ammonia, ammonium carbonate, ammonium bicarbonate, diammonium hydrogen phosphate, ammonium dihydrogen phosphate, and ammonium acetate; and the polyphosphoric acid or a salt thereof is selected from the group consisting of one or more of sodium polyphosphate, potassium polyphosphate, and ammonium polyphosphate.

Preferably, in the above technical solution, the GshF enzyme, the ATP regeneration enzyme and the AK enzyme are free or immobilized enzymes; the concentration of GshF enzyme is 0.01-10000 U/L, and the concentration of AK enzyme is 0.01-8000 U/L, wherein the completed conversion of 1 μM substrate within 1 minute is defined as 1 active unit (U). The ATP regeneration enzyme is a combination of any two or three of polyphosphate kinase (PPK), adenylate kinase (ADK) and polyphosphate: AMP phosphotransferase (PAP), and the concentration of PPK enzyme is 0.01-5000 U/L, the concentration of ADK enzyme is 0.01-5000 U/L, and the concentration of PAP enzyme is 0.01-5000 U/L. The above GshF enzyme, ATP regeneration enzyme and AK enzyme may be derived from any organism or an enzyme that has been artificially engineered to have the same catalytic function.

Preferably, in the above technical solution, when the production amount of GSH is about 30-40 g/L, the addition amount of GshF enzyme is preferably 750-1000 U/L, the addition amount of each regeneration enzyme is preferably 500 U/L, and the addition amount of AK enzyme is preferably 750-1000.

Preferably, in the above technical solution, the immobilized GshF enzyme, ATP regeneration enzyme and AK enzyme are immobilized on the immobilization carrier by the following mode: adsorption, crosslinking, covalent bonding, encapsulation or a combination thereof.

Preferably, in the above technical solution, the ultrafiltration membrane used is selected from the group consisting of a cellulose acetate membrane, a polysulfone membrane, a polyacrylonitrile membrane, a polyvinyl chloride membrane, a polyvinylidene fluoride membrane, a polyamide membrane or a ceramic membrane.

In the present invention adenosine is instead of ATP for preparing glutathione. The principle is to add adenosine kinase (AK, EC 2.7.1.20) to the original reaction system containing GshF and ATP regeneration enzyme which can catalyze adenosine to produce AMP, and in combination with the other ATP regeneration enzymes described above, under certain conditions, the enzymatic reaction for producing GSH can be carried out by only adding a small amount of adenosine without using ATP. Due to the improvement of the enzymatic production process, the composition of the reaction solution has changed greatly, the production amount of GSH is greatly increased, and the content of substances such as ATP and the like is greatly reduced. In addition, the concentration of ions such as magnesium ion and the like in the reaction solution also has changed, and the original GSH purification method is no longer suitable for the purification of the product prepared by the novel enzymatic method. The GSH produced by the enzymatic reaction of the present invention can be separated and purified by the purification method of the present invention, and it can be finally made into a dried crystalline powder, and the purity thereof can reach 98% or more.

Compared with the prior art, the technology of the present invention has the following beneficial effects:

1) the use of adenosine instead of ATP or AMP greatly reduces the cost of industrial production. The price of adenosine is only about 10% of ATP or 30% of AMP, adenosine is cheaper and has abundant sources, and its usage amount in the reaction can be optimized to be less than 10% of that of the previous ATP; 2) reaction conditions of GSH production are optimized, the composition of the reaction solution is specific and stable, the generation concentration of GSH can reach 30-50 g/L, the reaction rate is fast, and the conversion rate is high; 3) a stable enzyme recovery system has been established, and both the immobilized enzyme and the free enzyme can be recycled during the whole reaction process, and it is low in cost, energy saving and environment friendly after being applied to large-scale continuous production; 4) a small amount of by-products ATP, ADP and AMP can be either directly used for the cyclic reaction, or intensively collected for the production of ATP, or purified by filtration, ion exchange, etc., therefore, the operation is simple, and the purified product can be used as an additional product, thereby having certain economic benefits; 5) a purification process is established targeting the reaction solution of the present invention, the process is simple and effective, and the GSH can be purified to a purity of 98% or more, and by adding a filtration step of activated charcoal and the like, the GSH can be purified to a pharmaceutical grade; and 6) no heavy metal ions are added throughout the preparation process of the pure product from enzymatic reaction step to the dried step, except that ethanol is required to add to crystallize GSH for some processes, no other organic solvents are added, so the pollution is less.

DETAILED DESCRIPTION OF THE EMBODIMENTS

The specific examples of the present invention are described in detail below in combination with the accompanying drawings, in order to further understand the present invention. The various materials used in the following examples and comparative examples of the present invention can be obtained commercially, unless otherwise specified.

Example 1

Preparation of Crude Enzyme

The GshF enzyme, ATP regeneration enzyme and AK enzyme in the method of the present invention are commercially available, or are enzymes that have been artificially engineered to have the same catalytic function.

The preparation process of the enzyme is as follows:

Primers were designed based on the gene sequences of each of GshF enzyme, PPK enzyme, ADK enzyme, PAP enzyme and AK enzyme, and the gene fragments were amplified by PCR and ligated to the pET22b plasmid (commercially available), respectively, and respectively transferred to *E. coli* BL21 (DE3) strain (commercially available) after correct sequencing.

The transformed *E. coli* BL21 (DE3) monoclone was inoculated into LB medium, and after incubation in the logarithmic phase, 1 mM isopropyl-β-D-thiogalactopyranoside (IPTG) was added for induction. The bacteria were harvested after 5 hours of induction, and the high expression strains were screened using sodium dodecyl sulfate-polyacrylamide gel electrophoresis (SDS-PAGE).

The selected high expression strains were inoculated into the seed culture medium under sterile conditions, cultured in the logarithmic phase, and then amplificated into a fermenter containing 500 L of fermentation medium. After the OD600 value reached 20, 1 mM IPTG was added for 5 hours of induction, and the bacteria were finally harvested by centrifugation.

The composition of LB medium was: 1% peptone, 0.5% yeast extract powder and 1% NaCl; the composition of the seed medium was: 1% peptone, 0.5% yeast extract powder and 1% sodium chloride; and the composition of the fermentation medium was: 1% peptone 0.5% yeast extract powder, 1% sodium chloride, 5% disodium hydrogen phosphate, 1% sodium dihydrogen phosphate, 0.01% magnesium sulfate and 1% glycerol.

Figure 1:
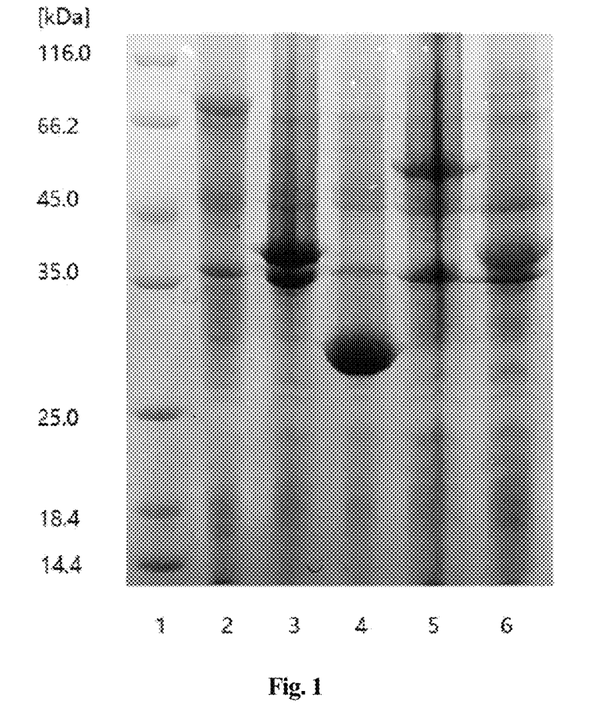
FIG. 1 is an SDS-PAGE diagram of the GshF enzyme, ATP regeneration enzyme and AK enzyme used in the present invention.

FIG. 1 is an SDS-PAGE diagram of *Escherichia coli* expressed GshF enzyme, PPK enzyme, ADK enzyme, PAP enzyme and AK enzyme. As shown in FIG. 1: Lane 1 was the protein marker 14.4-116 kDa (commercially available); Lane 2 was the GshF enzyme, 85 kDa; Lane 3 was the PPK enzyme, 40 kDa; Lane 4 was the ADK enzyme, 25 kDa; Lane 5 was a PAP enzyme, 55 kDa; and Lane 6 was an AK enzyme, 40 kDa.

After the harvested bacteria were homogenized and crushed under ultrasound or high pressure, the supernatant was collected by centrifugation. The crude enzyme was obtained by precipitation and filtration methods. The crude enzyme solution simultaneously contains a trace amount of ATP, and the reaction can be started without additional ATP, and the operation was more convenient.

Example 2

Preparation of GSH Using Free Enzyme

Figure 2:
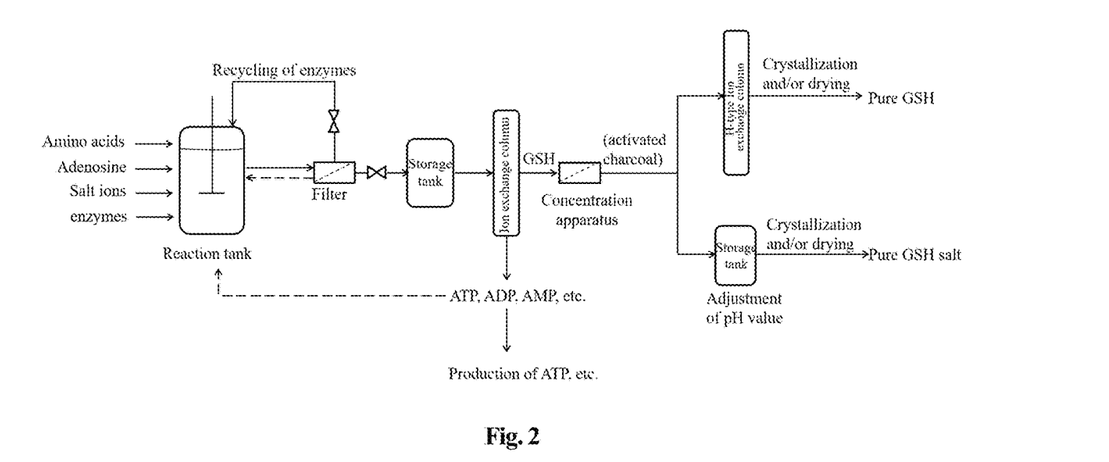
FIG. 2 is a schematic view showing the process flow for preparing GSH using a free enzyme in the present invention.

As shown in FIG. 2, the preparation of GSH using free enzymes includes the following steps:

(1) Generation of GSH in the reaction tank:

in the reaction tank, 100 L of the reaction system was a solution containing substrate 2.5 kg of glutamic acid, 2.5 kg of cysteine and 1.5 kg of glycine, 0.3 kg of adenosine, and 2.5 kg of sodium hexametaphosphate, 0.2 kg of ammonium sulfate, 0.3 kg of sodium chloride, 0.5 kg of magnesium chloride hexahydrate, 0.1 kg of manganese chloride monohydrate and 0.5 kg of disodium hydrogen phosphate, and the solution was uniformly stirred when formulated to prevent precipitation. The pH was adjusted to 7.0, and GshF enzyme 800 U/L, PPK enzyme 500 U/L, ADK enzyme 500 U/L, PAP enzyme 200 U/L and AK enzyme 600 U/L were added to the reaction system to start the reaction, and the enzymes added were all crude enzyme solutions. The pH value was controlled to 7.0 during the reaction and the temperature was 37° C.

Figure 4:
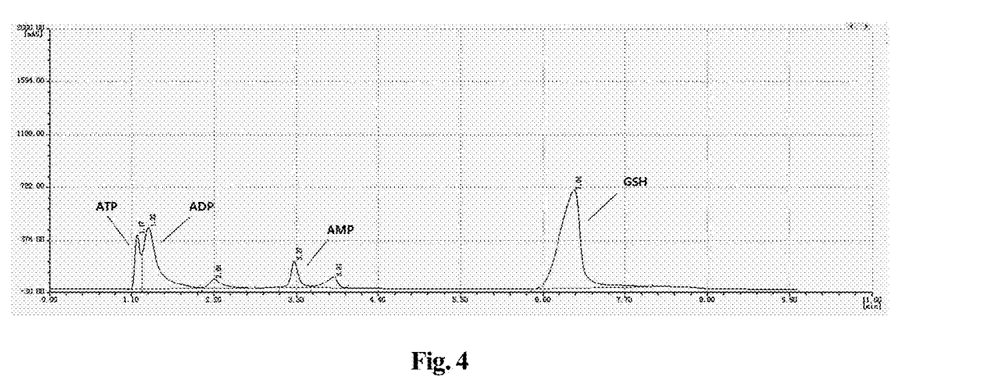
FIG. 4 is an HPLC spectrum of Example 2 of the present invention.

FIG. 4 is an HPLC spectrum of Example 2 of the present invention. As shown in FIG. 4, after 5 hours of reaction, the production amount of glutathione was detected by high performance liquid chromatography (HPLC) to be 35 g/L, and the non-indicated peaks in the figure were amino acid and the like.

The detection conditions of HPLC were as follows: Kromasil C18 chromatographic column (purchased from AKZO NOBEL) (150×4.6 mm), detection wavelength of 210 nm, and detection temperature of 25° C. The mobile phase was an aqueous solution containing 6.8 g/L of potassium dihydrogen phosphate, 2.0 g/L of sodium heptanesulfonate and 3% methanol, pH=3.0.

(2) Separation of the enzyme in the filter:

the reaction solution of step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution after the enzyme was separated.

(3) Separation products GSH and other substances:

the pH of the filtrate was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP. The through-liquid was collected for the production of ATP or further purified to obtain pure ATP, ADP and AMP.

The GSH on the cation exchange resin was eluted with a gradient of 0-0.8 M NaCl, and the production amount of GSH was 3.2 kg with a yield of 90%.

(4) A continuous reaction for generating GSH in the reaction tank, that is, a continuous reaction of step (1):

the enzyme separated in step (2) was added to the reaction tank through a reflux port of the filter, and a new enzyme having a concentration of 5-10% of the original enzyme was added for the reaction. The reaction solution was formulated in the same manner as in the above step (1).

The continuous reaction for producing GSH was carried out under the conditions of a pH 7.0 at 37° C.; after 5 hours, the production amount of GSH detected by HPLC was 32 g/L.

The HPLC detection conditions were the same as those in the above step (1). In this step, the enzyme was recycled.

Example 3

Preparation of GSH Using Free Enzyme

As shown in FIG. 2, the preparation of GSH using free enzymes includes the following steps:

(1) Generation of GSH in the reaction tank:

in the reaction tank, 100 L of the reaction system was a solution containing substrate 2.0 kg of glutamic acid, 2.0 kg of cysteine hydrochloride and 2.0 kg of glycine, 0.2 kg of adenosine, and 1.5 kg of sodium hexametaphosphate, 0.2 kg of ammonium chloride, 0.2 kg of potassium chloride, 0.8 kg of magnesium chloride hexahydrate, and 0.3 kg of Tris, and the solution was uniformly stirred when formulated to prevent precipitation. The pH was adjusted to 7.4, and GshF enzyme 1000 U/L, PPK enzyme 300 U/L, ADK enzyme 300 U/L, and AK enzyme 500 U/L were added to the reaction system to start the reaction, and the enzymes added were all crude enzyme solutions. The pH value was controlled to 7.4 during the reaction and the temperature was 40° C.

After 6 hours of reaction, the production amount of glutathione was detected by high performance liquid chromatography (HPLC) to be 30 g/L. The HPLC detection conditions were the same as those in step (1) of Example 2.

(2) Separation of the enzyme in the filter:

the reaction solution of step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution after the enzyme was separated.

(3) Separation products GSH and other substances:

the pH of the filtrate was adjusted to 3.0 with hydrochloric acid, and passed through the D001 macroporous strong acid styrene cation exchange resin in the ion exchange column.

The GSH, a part of amino acids and cations in the solution were adsorbed, and the through-liquid mainly contained ATP, ADP and AMP.

The GSH on the cation exchange resin was eluted with a gradient of 0-0.8 M NaCl, and the production amount of GSH was 2.7 kg with a yield of 90%.

(4) A continuous reaction for generating GSH in the reaction tank, that is, a continuous reaction of step (1):

the enzyme separated in step (2) was added to the reaction tank through a reflux port of the filter, and a new enzyme having a concentration of 5-10% of the original enzyme was added for the reaction. The ion exchanged through-liquid in step (3) was added to the reaction tank for solution formulation, and the formulation method of the reaction solution was the same as that in the above step (1), and the addition amount of adenosine was reduced to 0.03 kg.

The continuous reaction for producing GSH was carried out under the conditions of a pH 7.4 at 40° C.; after 6 hours, the production amount of GSH detected by HPLC was 30 g/L. The HPLC detection conditions were the same as those in step (1) of Example 2. In this step, the enzyme was recycled, and by-products such as ATP and the like generated in the previous cycle were recycled.

Example 4

Preparation of GSH Using Immobilized Enzyme

Figure 3:
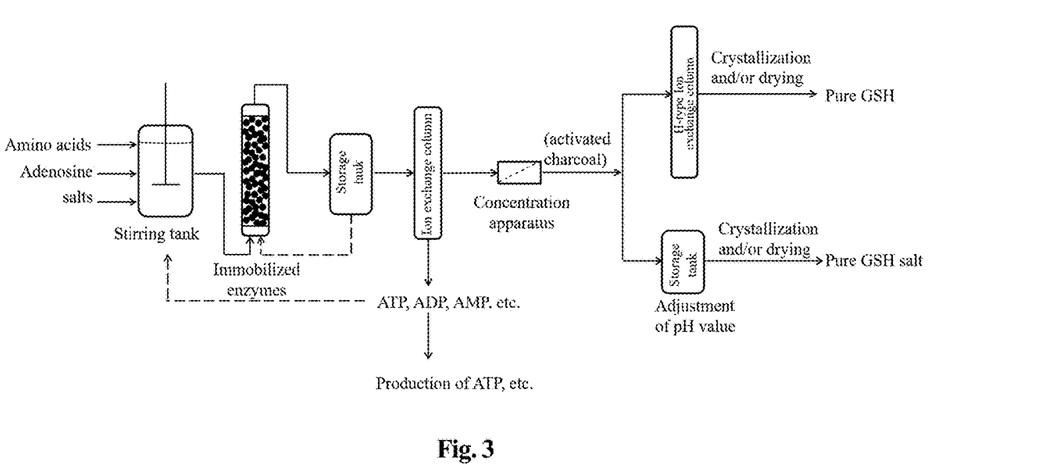
FIG. 3 is a schematic view showing the process flow for preparing GSH using an immobilized enzyme in the present invention.

As shown in FIG. 3, the preparation of GSH using immobilized enzyme includes the following steps:

(1) Immobilization of the enzyme the GshF enzyme, ADK enzyme, PAP enzyme and AK enzyme for catalysis were immobilized with a commercial amino-containing synthetic polymer carrier LX1000HA.

The crude enzyme GshF enzyme 4000 U/L described in the above Example 1 was added with 2 kg of LX1000HA wet carrier in a constant temperature stirring reaction tank, and stirred at 150 rpm for 12 hours at 20° C. The carrier was collected by filtration and washed twice with 0.02 M potassium phosphate buffer (pH 8.0) to obtain an immobilized GshF enzyme.

1000 U/L of ADK enzyme, 1200 U/L of PAP enzyme, and 3000 U/L of AK enzyme were separately immobilized on the LX1000HA carrier in the same manner.

(2) Generation of glutathione GSH in the reaction column:

the reaction solution was formulated, each 100 L of the reaction system was a solution containing substrate 2.5 kg of glutamic acid, 2.5 kg of cysteine and 2.0 kg of glycine, 0.3 kg of adenosine, and 2.2 kg of sodium polyphosphate, 0.3 kg of ammonium chloride, 0.6 kg of magnesium chloride hexahydrate, 0.1 kg of manganese chloride monohydrate and 0.6 kg of potassium dihydrogen phosphate, and the solution was uniformly stirred when formulated to prevent precipitation. The pH was adjusted to 7.3 and the temperature was raised to 42-45° C.

The enzyme reaction column was prepared by charging 20 kg of the immobilized enzyme in step (1) into the reaction column apparatus and exhausting the bubbles. The reaction solution was slowly passed through the enzyme reaction column from bottom to top at a flow rate of 20 L/h using a constant flow pump, and the temperature was controlled at 42-45° C. during the reaction. After 6 hours of reaction, the reaction solution was collected, and the production amount of glutathione was detected by high performance liquid chromatography (HPLC) to be 33 g/L. The HPLC detection conditions were the same as those in step (1) of Example 2.

(3) Separation products GSH and other substances:

the pH value of the reaction solution was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP. The through-liquid was collected for the production of ATP or further purified to obtain pure ATP, ADP and AMP.

The GSH on the cation exchange resin was eluted with a gradient of 0-0.8 M NaCl, and the production amount of GSH was 3.0 kg with a yield of 90%.

(3) A continuous reaction for generating GSH in the reaction column, that is, a continuous reaction of step (2):

the same reaction solution as described in step (2) was formulated, and continuously passed through the enzyme reaction column at a flow rate of 20 L/h from bottom to top, and the temperature during the reaction was controlled at 42 to 45° C.

After 6 hours of reaction, the production amount of GSH was detected by HPLC to be 33 g/L. The HPLC detection conditions were the same as those in step (1) of Example 2. In this step, the enzyme was recycled.

After the immobilized enzyme was circularly reacted for more than 20 times or stored at −4° C. for more than one month, the enzyme activity was reduced by 10%, therefore a part of new enzymes was needed to be added or replaced in proportion.

Example 5

Preparation of GSH Using Immobilized Enzyme

As shown in FIG. 3, the preparation of GSH using immobilized enzyme includes the following steps:

(1) Immobilization of the enzyme

The GshF enzyme, PPK enzyme, PAP enzyme and AK enzyme for catalysis were immobilized with a commercial epoxy immobilization carrier LX1000EP.

The crude enzyme GshF enzyme 8000 U/L, PPK enzyme 2000 U/L, PAP enzyme 2000 U/L and AK enzyme 5000 U/L described in the above Example 1 were mixed to formulate a mixed enzyme solution. The LX1000EP wet carrier was added to the constant temperature stirring reaction tank, and mixed with the above enzyme solution at a mass ratio of the immobilization carrier to the enzyme of 30:1, and stirred at 150 rpm for 12 hours at 20° C. The carrier was collected by filtration and washed twice with 0.02 M potassium phosphate buffer (pH 8.0) to obtain an immobilized mixed enzyme.

(2) Generation of glutathione GSH in the reaction column:

the reaction solution was formulated, each 100 L of the reaction system was a solution containing substrate 3.5 kg of glutamic acid, 3.2 kg of cysteine and 3.3 kg of glycine, 0.5 kg of adenosine, and 3.0 kg of sodium hexametaphosphate, 0.3 kg of sodium chloride, 0.8 kg of magnesium chloride hexahydrate, and 0.6 kg of potassium dihydrogen phosphate, and the solution was uniformly stirred when formulated to prevent precipitation. The pH was adjusted to 7.5 and the temperature was raised to 37-40° C.

The enzyme reaction column was prepared by charging 20 kg of the mixed immobilized enzyme in step (1) into the reaction column apparatus and exhausting the bubbles. The reaction solution was slowly passed through the enzyme reaction column from bottom to top at a flow rate of 20 L/h using a constant flow pump, and the temperature was controlled at 37-40° C. during the reaction. After 6 hours of reaction, the reaction solution was collected, and the production amount of glutathione was detected by high performance liquid chromatography (HPLC) to be 40 g/L. The HPLC detection conditions were the same as those in step (1) of Example 2.

(3) Separation products GSH and other substances:

The pH value of the reaction solution was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP. The through-liquid was collected for the production of ATP or further purified to obtain pure ATP, ADP and AMP.

The GSH on the cation exchange resin was eluted with a gradient of 0-0.8 M NaCl, and the production amount of GSH was 3.5 kg with a yield of 85%.

(3) A continuous reaction for generating GSH in the reaction column, that is, a continuous reaction of step (2):

the same reaction solution as described in step (2) was formulated, and continuously passed through the enzyme reaction column at a flow rate of 20 L/h from bottom to top, and the temperature during the reaction was controlled at 37 to 40° C.

After 6 hours of reaction, the production amount of GSH was detected by HPLC to be 40 g/L. The HPLC detection conditions were the same as those in step (1) of Example 2. In this step, the enzyme was recycled.

After the immobilized enzyme was circularly reacted for more than 20 times or stored at -4° C. for more than one month, the enzyme activity was reduced by 10%, therefore a part of new enzymes was needed to be added or replaced in proportion.

Example 6

As shown in FIG. 2, the preparation of GSH using free enzymes includes the following steps:

(1) Generation of GSH in the reaction tank:

in the reaction tank, 100 L of the reaction system was a solution containing substrate 0.1 kg of glutamic acid, 0.1 kg of cysteine and 0.05 kg of glycine, 0.001 kg of adenosine, and 0.47 kg of polyphosphoric acid, 0.066 kg of ammonium sulfate, 0.074 kg of potassium chloride, 0.2 kg of magnesium chloride hexahydrate, and 0.12 kg of Tris, and the solution was uniformly stirred when formulated to prevent precipitation. The pH was adjusted to 10.0, and GshF enzyme 0.01 U/L, PPK enzyme 0.01 U/L, ADK enzyme 0.01 U/L, PAP enzyme 0.01 U/L and AK enzyme 0.01 U/L were added to the reaction system to start the reaction, and the enzymes added were all crude enzyme solutions. The pH value was controlled to 10.0 during the reaction and the temperature was 25° C.

After 8 hours of reaction, the production amount of glutathione was detected by high performance liquid chromatography (HPLC) to be 0.6 g/L. The HPLC detection conditions were the same as those in step (1) of Example 2.

(2) Separation of the enzyme in the filter:

the reaction solution of step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution after the enzyme was separated.

(3) Separation products GSH and other substances:

the pH of the filtrate was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP. The through-liquid was collected for the production of ATP or further purified to obtain pure ATP, ADP and AMP.

The GSH on the cation exchange resin was eluted with a gradient of 0-0.8 M NaCl, and the production amount of GSH was 0.05 kg with a yield of 90%.

(4) A continuous reaction for generating GSH in the reaction tank, that is, a continuous reaction of step (1):

the enzyme separated in step (2) was added to the reaction tank through a reflux port of the filter, and a new enzyme having a concentration of 30-50% of the original enzyme was added for the reaction. The reaction solution was formulated in the same manner as in the above step (1).

The continuous reaction for producing GSH was carried out under the conditions of a pH 10.0 at 25° C.; after 8 hours, the production amount of GSH detected by HPLC was 0.6 g/L.

The HPLC detection conditions were the same as those in the above step (1). In this step, the enzyme was recycled.

Example 7

As shown in FIG. 2, the preparation of GSH using free enzymes includes the following steps:

(1) Generation of GSH in the reaction tank:

in the reaction tank, 100 L of the reaction system was a solution containing substrate 8.0 kg of glutamic acid, 5.0 kg of cysteine and 7.5 kg of glycine, 2.0 kg of adenosine, and 14.1 kg of polyphosphoric acid, 2.93 kg of sodium chloride, 4.07 kg of magnesium chloride hexahydrate, and 1.75 kg of dipotassium hydrogen phosphate, and the solution was uniformly stirred when formulated to prevent precipitation. The pH was adjusted to 5.0, and GshF enzyme 5000 U/L, PPK enzyme 2500 U/L, ADK enzyme 2500 U/L, PAP enzyme 2500 U/L and AK enzyme 4000 U/L were added to the reaction system to start the reaction, and the enzymes added were all crude enzyme solutions. The pH value was controlled to 5.0 during the reaction and the temperature was 50° C.

After 8 hours of reaction, the production amount of glutathione was detected by high performance liquid chromatography (HPLC) to be 29 g/L. The HPLC detection conditions were the same as those in step (1) of Example 2.

(2) Separation of the enzyme in the filter:

The reaction solution of step (1) was passed through a filter to separate the mixed enzyme by an ultrafiltration method, and a membrane package (purchased from Pall Corporation, with a molecular weight cut off of 20 kDa) was placed in the filter, and the filtrate was a reaction solution after the enzyme was separated.

(3) Separation products GSH and other substances:

the pH of the filtrate was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP. The through-liquid was collected for the production of ATP or further purified to obtain pure ATP, ADP and AMP.

The GSH on the cation exchange resin was eluted with a gradient of 0-0.8 M NaCl, and the production amount of GSH was 2.6 kg with a yield of 90%.

(4) A continuous reaction for generating GSH in the reaction tank, that is, a continuous reaction of step (1):

the enzyme separated in step (2) was added to the reaction tank through a reflux port of the filter, and a new enzyme having a concentration of 15-30% of the original enzyme was added for the reaction. The reaction solution was formulated in the same manner as in the above step (1).

The continuous reaction for producing GSH was carried out under the conditions of a pH 5.0 at 50° C.; after 8 hours, the production amount of GSH detected by HPLC was 29 g/L. The HPLC detection conditions were the same as those in the above step (1). In this step, the enzyme was recycled.

Example 8

As shown in FIG. 3, the preparation of GSH using immobilized enzymes includes the following steps:

(1) Immobilization of the enzyme the GshF enzyme, PPK enzyme, ADK enzyme, PAP enzyme and AK enzyme for catalysis were immobilized with a commercial amino-containing synthetic polymer carrier LX1000HA.

The crude enzyme GshF enzyme 10000 U/L described in the above Example 1 was added with 2 kg of LX1000HA wet carrier in a constant temperature stirring reaction tank, and stirred at 150 rpm for 12 hours at 20° C. The carrier was collected by filtration and washed twice with 0.02 M potassium phosphate buffer (pH 8.0) to obtain an immobilized GshF enzyme. 5000 U/L of PPK enzyme, 5000 U/L of ADK enzyme, 5000 U/L of PAP enzyme, and 8000 U/L of AK enzyme were separately immobilized on the LX1000HA carrier in the same manner.

(2) Generation of glutathione GSH in the reaction column:

the reaction solution was formulated, each 100 L of the reaction system was a solution containing substrate 5.0 kg of glutamic acid, 2.0 kg of cysteine and 3.0 kg of glycine, 2.0 kg of adenosine, and 3.0 kg of sodium hexametaphosphate, 3.73 kg of potassium chloride, 2.16 kg of manganese chloride monohydrate, and 1.56 kg of sodium dihydrogen phosphate dihydrate, and the solution was uniformly stirred when formulated to prevent precipitation. The pH was adjusted to 6.0 and the temperature was raised to 55° C.

The enzyme reaction column was prepared by charging 20 kg of the immobilized enzyme in step (1) into the reaction column apparatus and exhausting the bubbles. The reaction solution was slowly passed through the enzyme reaction column from bottom to top at a flow rate of 20 L/h using a constant flow pump, and the temperature was controlled at 55° C. during the reaction. After 6 hours of reaction, the reaction solution was collected, and the production amount of glutathione was detected by high performance liquid chromatography (HPLC) to be 28 g/L. The HPLC detection conditions were the same as those in step (1) of Example 2.

(3) Separation products GSH and other substances:

the pH value of the reaction solution was adjusted to 3.0 with hydrochloric acid, and passed through the D001 macroporous strong acid styrene cation exchange resin in the ion exchange column. The GSH, a part of amino acids and cations in the solution were adsorbed, and the through-liquid mainly contained ATP, ADP and AMP. The through-liquid was collected for the production of ATP or further purified to obtain pure ATP, ADP and AMP.

The GSH on the cation exchange resin was eluted with a gradient of 0-0.8 M NaCl, and the production amount of GSH was 2.6 kg with a yield of 90%.

(3) A continuous reaction for generating GSH in the reaction column, that is, a continuous reaction of step (2):

the same reaction solution as described in step (2) was formulated, and continuously passed through the enzyme reaction column at a flow rate of 20 L/h from bottom to top, and the temperature during the reaction was controlled at 55° C.

After 6 hours of reaction, the production amount of GSH was detected by HPLC to be 28 g/L. The HPLC detection conditions were the same as those in step (1) of Example 2. In this step, the enzyme was recycled.

After the immobilized enzyme was circularly reacted for more than 20 times or stored at −4° C. for more than one month, the enzyme activity was reduced by 40%, therefore a part of new enzymes was needed to be added or replaced in proportion.

Example 9

The reaction solution was formulated, the concentrations of the three amino acids were 25 g/L of glutamic acid, 25 g/L of cysteine, and 15 g/L of glycine, and the concentrations of other major substances were 5 g/L of adenosine, 25 g/L of sodium hexametaphosphate, 2 g/L of ammonium sulfate, 5 g/L of magnesium chloride hexahydrate and 2 g/L of manganese chloride monohydrate, and the pH value was adjusted using sodium hydroxide to 7.0. Different amounts of GshF enzyme, PPK enzyme, ADK enzyme, PAP enzyme and AK enzyme were added to carry out the reaction, and the pH value was controlled at 7.0 and the temperature was controlled at 37° C. during the reaction. Data of the maximum value of GSH in each reaction were recorded (Table 1).

TABLE 1

Comparative Data for Enzymes Used in the Reaction

| No. | Usage amount of enzyme [U/L] | | | | | Maximum value of the generated GSH [g/L] | Reaction time [h] |
| --- | --- | --- | --- | --- | --- | --- | --- |
| | GshF | PPK | ADK | PAP | AK | | |
| 1 | 250 | 1000 | 1000 | 1000 | 1000 | 27.5 | 8 |
| 2 | 500 | 1000 | 1000 | 1000 | 1000 | 33 | 7 |
| 3 | 750 | 1000 | 1000 | 1000 | 1000 | 36 | 5.5 |
| 4 | 1000 | 1000 | 1000 | 1000 | 1000 | 35.8 | 5 |
| 5 | 1500 | 1000 | 1000 | 1000 | 1000 | 35.5 | 4 |
| 6 | 1000 | 250 | 250 | 250 | 250 | 31 | 5.5 |
| 7 | 1000 | 500 | 500 | 500 | 500 | 36 | 5.5 |
| 8 | 1000 | 500 | 500 | | 500 | 35.7 | 5.5 |
| 9 | 1000 | | 500 | 500 | 500 | 36.1 | 5.5 |
| 10 | 1000 | 500 | | 500 | 500 | 35 | 5.5 |
| 11 | 1000 | 500 | 500 | 500 | 750 | 36 | 5 |
| 12 | 1000 | 500 | 500 | 500 | 1000 | 35.9 | 5 |

In the reactions 1-5 listed in Table 1, the addition amount of regeneration enzyme is excessive, and the ATP production/regeneration rate can fully meet the needs of GSH production. As the amount of GshF enzyme is too low, the production amount of GSH is low and the reaction rate is slow, when the amount of GshF is too high, although the reaction rate is high, after reaching the maximum production amount, the GSH may be decomposed, causing decreased yield.

The comparison of the reactions 5-7 listed in Table 1 shows that the usage amount of regeneration enzyme and AK enzyme affects the rate of ATP production/regeneration and also the production amount of GSH.

The comparison of the reactions 7-10 listed in Table 1 shows that among the ATP regeneration enzymes, the selection of the combination of PPK, ADK and PAP, or the combination of PPK and ADK, or the combination of PAP and ADK, or the combination of PPK and PAP, has little difference in regeneration effect.

The comparison of the reactions 10-12 listed in Table 1 shows that when the usage amount of AK enzyme is increased within a certain range, the reaction rate is increased, especially the reaction rate is increased in the initial stage.

When the production amount of GSH was about 30-40 g/L by using the above reaction solution, the addition amount of GshF enzyme was preferably 750-1000 U/L, and the addition amount of each regeneration enzyme was preferably 500 U/L, and the addition amount of AK enzyme was preferably 750-1000.

Example 10

Scale Up in Tons

The reaction was scaled up in tons, and the reaction and purification steps were as follows:

(1) In the reaction tank, 1000 L of the reaction system was a solution containing substrate 25.0 kg of glutamic acid, 25.0 kg of cysteine and 15.0 kg of glycine, 5.0 kg of adenosine, and 25.0 kg of sodium hexametaphosphate, 10.0 kg of ammonium sulfate, 5.2 kg of magnesium chloride hexahydrate, and 1.0 kg of manganese chloride monohydrate, and the solution was uniformly stirred when formulated to prevent precipitation. The pH was adjusted to 7.0, and GshF enzyme 1000 U/L, PPK enzyme 500 U/L, ADK enzyme 500 U/L, PAP enzyme 500 U/L and AK enzyme 750 U/L were added to the reaction system to start the reaction, and the enzymes added were all crude enzyme solutions. The pH value was controlled to 7.0 during the reaction and the temperature was 37° C.

After 6 hours of reaction, the production amount of glutathione was detected by high performance liquid chromatography (HPLC) to be 36.4 g/L, and the HPLC detection conditions were the same as those in step (1) of Example 2.

(2) Separation of the enzymes using an ultrafiltration apparatus:

the reaction solution from step (1) was filtered using an ultrafiltration apparatus, and the interception size of the ultrafiltration membrane was 5 kDa, and the filtrate and the retentate were separately collected. The filtrate was a reaction solution containing the product after separation of the enzyme, and the retentate was a recovered enzyme solution.

(3) Ion exchange chromatography:

The pH value of the filtrate from the above step was adjusted to 3.0, passed through the cation exchange resin containing a sulfonic group (commercially available), and after the loading of the sample was finished, it was first washed with pure water. The through-liquid and top washing liquid mainly contained ATP, ADP, AMP and phosphate; it was then eluted with 40 mM ammonium chloride to mainly remove the impurities such as amino acids; and then the GSH was eluted with a mixed solution containing 100 mM of ammonium chloride and 30 mM of hydrochloric acid, and the through-liquid from this step was collected.

The solution containing the ATP, ADP and AMP fractions was separated to produce GSH, or to produce ATP or further purified to obtain pure ATP, ADP and AMP.

(4) Concentration

The eluate containing GSH from the previous step was concentrated using a nanofiltration apparatus, and the cut-off molecular weight of the nanofiltration membrane was 200, and the retentate was collected. The nanofiltration retentate was concentrated using a vacuum concentration apparatus, and the degree of vacuum was about −0.09 MPa to a concentration of GSH of 200 g/L or more.

(5) 0.5% activated charcoal was added to remove endotoxin, and the filtrate was collected by filtration.

(6) The solution from the previous step was passed through a 5% hydrochloric acid-treated cation exchange resin containing aminophosphonic acid (commercially available) to convert GSH to an H form, and the through-liquid was collected.

(7) Ethanol was added until an ethanol concentration was 70%, and allowed to stand at 15° C. for 12 hours, during which it was stirred slowly. The crystals were collected by filtration and washed with ethanol.

(8) After the crystals were collected, they were placed in a drying oven, the temperature was controlled at 45° C., the crystals were vacuum-dried under reduced pressure for 12 hours, with a degree of vacuum of about −0.08 MPa, and 29.9 kg of dry powder was collected, and the overall yield of purification was 82%.

(9) The retentate from step (2) was added to the reaction tank, and new enzyme in an amount of 5-10% of the original enzyme was added to carry out the reaction. The reaction solution was formulated in the same manner as in the above step (1). After 6 hours of reaction, the production amount of glutathione was detected by high performance liquid chromatography (HPLC) to be 36.3 g/L, and the HPLC detection conditions were the same as those in step (1) of Example 2. In this step, the enzyme was recycled.

(10) Step (9) was repeated for 10-50 times, and the production amount of GSH remained basically unchanged.

Example 11

Aqueous ammonia was slowly added to the concentrate in step (4) of Example 10, and the pH value of the solution was adjusted to 5.8.

Under the reduced pressure, a gradient range of −30-20° C. of the temperature was controlled, and the GSH ammonium salt was obtained by lyophilization.

The overall yield of purification was about 80%.

Example 12

The (1) reaction step for preparing GSH and (2) the step of recovering the enzyme by filtration were the same as those in Example 10.

(3) The pH value of the filtrate was adjusted to 3.0, passed through the cation exchange resin containing a sulfonic group (commercially available), and after the loading of the sample was finished, it was first washed with pure water. The through-liquid and top washing liquid mainly contained ATP, ADP, AMP and phosphate; it was then eluted with 40 mM potassium chloride to mainly remove the impurities such as amino acids; and then the GSH was eluted with 100 mM of potassium chloride solution, and the through-liquid from this step was collected.

The solution containing the ATP, ADP and AMP fractions was separated to produce GSH, or to produce ATP or further purified to obtain pure ATP, ADP and AMP.

(4) Concentration

The eluate containing GSH from the previous step was concentrated using a nanofiltration apparatus, the cut-off molecular weight of the nanofiltration membrane was 200, and the retentate was collected. The nanofiltration retentate was concentrated using a vacuum concentration apparatus, and the degree of vacuum was about −0.09 MPa to a concentration of GSH of 200 g/L or more.

(5) Potassium hydroxide was slowly added to the concentrate from the previous step to adjust the pH value of the solution to 7.0.

(6) GSH potassium salt was obtained by spray drying, and the temperature at the air outlet of the spray drying tower was controlled to be below 80° C.

The overall yield of purification was about 85%.

Example 13

The reaction was scaled up in tons, and the reaction and purification steps were as follows:

(1) In the reaction tank, 1000 L of the reaction system was a solution containing substrate 5.0 kg of glutamic acid, 5.0 kg of cysteine and 5.0 kg of glycine, 5.0 kg of adenosine, and 25.0 kg of sodium hexametaphosphate, 10.0 kg of ammonium sulfate, 5.2 kg of magnesium chloride hexahydrate, and 1.0 kg of manganese chloride monohydrate, and the solution was uniformly stirred when formulated to prevent precipitation. The pH was adjusted to 7.0, and GshF enzyme 1000 U/L, ADK enzyme 500 U/L, PAP enzyme 500 U/L and AK enzyme 750 U/L were added to the reaction system to start the reaction, and the enzymes added were all crude enzyme solutions. After the reaction started, the amino acid solution was supplemented. The solution contained 20.0 kg of glutamic acid, 20.0 kg of cysteine and 10.0 kg of glycine, the supplementary rate was controlled to be completed within 6 hours, the pH value was controlled to 7.0 during the reaction, and the temperature was 37° C.

After 8 hours of reaction, the production amount of glutathione was detected by high performance liquid chromatography (HPLC) to be 37 g/L, and the HPLC detection conditions were the same as those in step (1) of Example 2.

(2) Separation of the enzymes using an ultrafiltration apparatus:

the reaction solution from step (1) was filtered using an ultrafiltration apparatus, and the interception size of the ultrafiltration membrane was 5 kDa, and the filtrate and the retentate were separately collected. The filtrate was a reaction solution containing the product after separation of the enzyme, and the retentate was a recovered enzyme solution.

(3) Ion exchange chromatography:

the pH value of the filtrate from the above step was adjusted to 3.0, passed through the cation exchange resin containing a carboxyl group (commercially available), and after the loading of the sample was finished, it was first washed with pure water. The through-liquid and top washing liquid mainly contained ATP, ADP, AMP and phosphate; it was then eluted with 50 mM sodium acetate to mainly remove the impurities such as amino acids; and then the GSH was eluted with a mixed solution containing 110 mM of sodium acetate and 40 mM of acetic acid, and the through-liquid from this step was collected.

The solution containing the ATP, ADP and AMP fractions was separated to produce ATP or further purified to obtain pure ATP, ADP and AMP. The yield of GSH in this step was about 90%.

(4) Concentration

The eluate containing GSH from the previous step was concentrated using a nanofiltration apparatus, the cut-off molecular weight of the nanofiltration membrane was 200, and the retentate was collected. The nanofiltration retentate was concentrated using a vacuum concentration apparatus, and the degree of vacuum was about −0.09 MPa to a concentration of GSH of 300 g/L or more.

(5) 0.01% activated charcoal was added to remove endotoxin, and the filtrate was collected by filtration.

(6) The solution from the previous step was passed through a 5% hydrochloric acid-treated cation exchange resin containing a sulfonic group (commercially available) to convert GSH to an H form, and the through-liquid was collected.

(7) Ethanol was added until an ethanol concentration was 40%, and allowed to stand at 0° C. for 6 hours, during which it was stirred slowly. The crystals were collected by filtration and washed with ethanol.

(8) After the crystals were collected, they were placed in a drying oven, the temperature was controlled at 45° C., the crystals were vacuum-dried under reduced pressure for 12 hours, with a degree of vacuum of about −0.08 MPa, and 31.5 kg of the dry powder was collected, and the overall yield of purification was 85%.

(9) The retentate from step (2) was added to the reaction tank, and new enzyme in an amount of 5-10% of the original enzyme was added to carry out the reaction. The ion exchanged through-liquid in step (3) was added to the reaction tank for solution formulation, and the formulation method of the reaction solution was the same as that in the above step (1), and the addition amount of adenosine was reduced to 0.5 kg. After 8 hours of reaction, the production amount of glutathione was detected by high performance liquid chromatography (HPLC) to be 37 g/L, and the HPLC detection conditions were the same as those in step (1) of Example 2. In this step, the enzyme was recycled.

(10) Step (9) was repeated for 10-50 times, and the production amount of GSH remained basically unchanged.

Example 14

The sodium hydroxide was slowly added to the concentrate in step (4) of Example 13, and the pH value of the solution was adjusted to 7.5.

Ethanol was added until an ethanol concentration was 60%, and allowed to stand at 5° C. for 12 hours, during which it was stirred slowly. The crystals were collected by filtration and washed with ethanol.

After the crystals were collected, they were placed in a drying oven, the temperature was controlled at 45° C., the crystals were vacuum-dried under reduced pressure for 16 hours, with a degree of vacuum of about −0.08 MPa, and 31.5 kg of the dry powder was collected, and the overall yield of purification was 85%.

Example 15

The purified finished product in Example 10 was tested, and the test results were as follows:

TABLE 2

Test Report of GSH

| Test items | | Standard | Test results |
|---|---|---|---|
| Appearance | | White or off-white, crystalline powder | White crystalline powder |
| Infrared identification | | The infrared spectrum should be consistent with the control spectrum | Consistent with the control spectrum |
| Specific optical rotation | | −15.5° to −17.5° | −15.8° |
| Clarity | | Colorless clear liquid | Colorless clear liquid |
| Related substances (HPLC) | Impurity A (L-cysteinyl glycine) | ≤0.5% | 0.1% |
| | Impurity B (cysteine) | ≤0.5% | 0.1% |
| | Impurity C (oxidized glutathione) | ≤1.5% | 0.3% |
| | Impurity D (L-γ-glutamyl-L-cysteine) | ≤1.0% | 0.5% |
| | Impurity E (degradation product) | ≤0.5% | 0.3% |
| | Total impurities | ≤2.5% | 1.5% |
| Chloride | | ≤200 ppm | Qualified |
| Sulfate | | ≤300 ppm | Qualified |
| Ammonium salt | | ≤200 ppm | Qualified |
| Iron | | ≤10 ppm | Qualified |
| Arsenic | | ≤1 ppm | Qualified |
| Heavy metals | | ≤10 ppm | Qualified |
| Burned residues | | ≤0.1% | 0.01% |
| Loss on drying | | ≤0.5% | 0.2% |
| Content | | 98.0% to 101.0% | 98.9% |

Comparative Example 1

In the reaction tank, 100 L of the reaction system was a solution containing substrate 2.5 kg of glutamic acid, 2.5 kg of cysteine and 1.5 kg of glycine, 16.0 kg of ATP, and 0.2 kg of ammonium sulfate, 0.3 kg of sodium chloride, 0.5 kg of magnesium chloride hexahydrate, 0.1 kg of manganese chloride monohydrate and 0.5 kg of disodium hydrogen phosphate, and the solution was uniformly stirred when formulated to prevent precipitation. The pH was adjusted to 7.0, GshF enzyme 800 U/L was added to the reaction system to start the reaction, and the enzyme added was crude enzyme solution. The pH value was controlled to 7.0 during the reaction and the temperature was 37° C.

Figure 5:
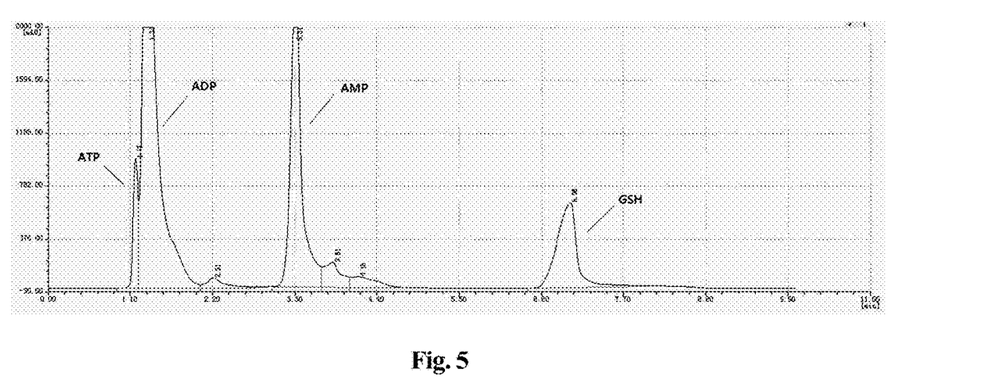
FIG. 5 is an HPLC spectrum of Comparative Example 1.

FIG. 5 is an HPLC spectrum of Comparative Example 1. As shown in FIG. 5, after 5 hours of reaction, the production amount of glutathione was detected by high performance liquid chromatography (HPLC) to be 32 g/L, and about 90% of ATP was depleted and converted into ADP and AMP. The non-indicated peaks in the figure were amino acid. The HPLC detection conditions were the same as those in step (1) of Example 2.

It can be seen from the results that in the Comparative Example 1, the ATP regeneration enzyme and the AK enzyme are not coupled, and a large amount of ATP is used for the reaction. The production amount of GSH within the same time is reduced, and the cost of raw materials is more than 100 times than that of the present patent.

Compared with Comparative Example 1, the present patent adds ATP regeneration enzyme and AK enzyme, and uses a small amount of adenosine instead of a large amount of ATP as an energy donor, thereby greatly reducing the cost of industrial production. By-products produced in the reaction are either recycled, or isolated and purified to pure products, so the operation is simple, or used for the production of ATP, and all the applications are very suitable for large-scale continuous production.

Although the present invention has been disclosed in the above embodiments, the above embodiments are not intended to limit the present invention, and various selections and modifications can be made without departing from the spirit and scope of the present invention by any person skilled in the art. Therefore, the protection scope of the present invention is defined by the claims and their equivalents.

What is claimed is:

1. An enzymatic method for preparing glutathione (GSH), comprising the following steps:
   (1) producing GSH in a reaction system using GshF enzyme, ATP regeneration enzyme, AK enzyme, wherein the reaction system comprises as substrates
       a combination of one or more of amino acid or a salt thereof;
       adenosine, wherein adenosine replaces the use of ATP and AMP such that no exogenous ATP or AMP is part of the substrates in the reaction system;
       polyphosphoric acid or a salt thereof; and
       magnesium ions or manganese ions;
   (2) separating the GshF enzyme by a method selected from the group consisting of:
       directly immobilizing the GshF enzyme, the ATP regeneration enzyme and the AK enzyme in the reaction vessel to separate the GshF enzyme in the reaction system; and
       separating free GshF enzyme using a filtration device to produce a filtrate;
   (3) separating the GshF enzyme obtained in step (2) by an ion exchange method to obtain a crude product GSH and a small amount of ATP, ADP and AMP, wherein the small amount of ATP, ADP and AMP are also products of the reaction system; and (4) subjecting the crude product GSH obtained in step (3) to concentration, crystallization, and drying to produce a finished GSH.

2. The method according to claim 1, wherein step (3) further comprises:
adjusting the pH value of the filtrate to be acidic;
passing the filtrate through a cation exchange resin containing a carboxyl or a sulfonic group; and
using a combination of one or more of sodium chloride, potassium chloride, ammonium chloride, sodium acetate, ammonium acetate, potassium acetate, hydrochloric acid, and acetic acid to stepwise elute crude product GSH and the small amount of ATP, ADP and AMP after adsorption;
wherein the small amount of ATP, ADP and AMP is optionally directly added to the reaction system or further separated and purified to obtain pure ATP, ADP and AMP.

3. The method according to claim 2, wherein step (4) comprises:
concentrating the crude product GSH to produce a GSH concentrate by at least one method selected from the group consisting of: nanofiltration concentration and vacuum concentration;
slowly adding sodium hydroxide, potassium hydroxide, or aqueous ammonia to the GSH concentrate and adjusting the pH to a range of 5.8-7.5, so that GSH can form a solution of sodium salt, potassium salt or ammonium salt; or passing the GSH concentrate through an H-type cation exchange resin containing an aminophosphonate or a sulfonic group to convert GSH to an H form, and collecting a through-liquid; and
obtaining a finished GSH by a method selected from the group consisting of: adding ethanol to the solution or the through-liquid, stirring to crystallize the GSH, collecting the crystals by filtration, washing the crystals with ethanol, vacuum drying under reduced pressure to obtain a finished GSH; directly spray-drying the solution or the through-liquid to obtain a GSH; and lyophilizing the solution or the through-liquid to obtain a finished GSH.

4. The method according to claim 1, further comprising at least one step selected from the group consisting of:
recycling the GshF enzyme, the ATP regeneration enzyme and the AK enzyme separated in step (2) by adding the separated GshF enzyme, the ATP regeneration enzyme and the AK enzyme into the reaction system for a continuous reaction of generating GSH; and
continuously separating the GshF enzyme, the ATP regeneration enzyme and the AK enzyme) by: continuously separating the immobilized GshF enzyme, ATP regeneration enzyme and AK enzyme; or continuously separating the free GshF enzyme, ATP regeneration enzyme and AK enzyme using a filtration device.

5. The method according to claim 1, wherein step (4) further comprises: removing endotoxin using activated charcoal, the activated charcoal being used at a concentration of 0.01-0.5%.

6. The method according to claim 1, wherein the reaction conditions for producing GSH in the reaction system in step (1) are as follows:
the reaction temperature is 25-55° C. or 30-50° C.;
the reaction pH is 5-10 or pH is 6-9;
and GshF enzyme, ATP regeneration enzyme and AK enzyme are added to the reaction system to react, so that GSH is produced.

7. The method according to claim 6, wherein the amino acid or a salt thereof is an L-amino acid or a salt thereof.

8. The method according to claim 7, wherein the amino acid or a salt thereof is glutamic acid or a salt thereof (Glu), cysteine or a salt thereof (Cys), and glycine or a salt thereof (Gly), wherein the addition mass ratio of the three amino acids is preferably as follows: Glu:Cys:Gly=(1-2.5): 1:(0.5-1.5) or Glu:Cys:Gly=(1.2-2):1:(0.8-1.5).

9. The method according to claim 7, wherein the amino acid or a salt thereof is glutamic acid or a salt thereof (Glu), cysteine or a salt thereof (Cys), and glycine or a salt thereof (Gly), wherein the addition concentration of cysteine (Cys) is 1-50 g/L.

10. The method according to claim 6, wherein:
the GshF enzyme, ATP regeneration enzyme and the AK enzyme are free or immobilized enzymes;
the concentration of GshF enzyme is 0.01-10000 U/L;
the concentration of AK enzyme is 0.01-8000 U/L; and
ATP regeneration enzyme is a combination of any two or three of polyphosphate kinase (PPK), adenylate kinase (ADK) and polyphosphate-adenylate phosphotransferase (PAP), and wherein the concentration of PPK enzyme is 0.01-5000 U/L, the concentration of ADK enzyme is 0.01-5000 U/L, and the concentration of PAP enzyme is 0.01-5000 U/L.

11. The method according to claim 6, wherein:
the concentration of adenosine is 0.01-20 g/L, preferably 0.01-5 g/L;
the concentration of polyphosphoric acid or a salt thereof is 0.01-0.3 M;
the concentration of magnesium ion is 0.01-0.2 M;
the concentration of manganese ion is 0.005-0.15 M;
the GshF enzyme, ATP regeneration enzyme and the AK enzyme are free or immobilized enzymes;
the concentration of GshF enzyme is 0.01-10000 U/L;
the concentration of AK enzyme is 0.01-8000 U/L; and
ATP regeneration enzyme is a combination of any two or three of polyphosphate kinase (PPK), adenylate kinase (ADK) and polyphosphate: AMP phosphotransferase (PAP), and wherein the concentration of PPK enzyme is 0.01-5000 U/L, the concentration of ADK enzyme is 0.01-5000 U/L, and the concentration of PAP enzyme is 0.01-5000 U/L.

12. The method according to claim 1, wherein the reaction system for producing GSH in the reaction tank in step (1) further comprises:
at least one member selected from the group consisting of sodium ions, potassium ions and ammonium ions; and
at least one member selected from the group consisting of one or two of Tris and aqueous solution of phosphate;
wherein the concentration of sodium ion is 0.01-0.5 M; the concentration of potassium ion is 0.01-0.5 M; the concentration of ammonium ion is 0.01-0.3 M; the concentration of Tris is 0.01-0.1 M; and the concentration of phosphate in the aqueous solution is 0.01-0.1 M.

13. An enzymatic method for preparing glutathione (GSH), comprising the following steps:
(1) producing GSH in a reaction system using GshF enzyme, ATP regeneration enzyme, and AK enzyme, wherein the step comprises:
adding 100 L of a solution into the reactor system, wherein the solution consists of:
2.5 kg of glutamic acid;
2.5 kg of cysteine;

1.5 kg of glycine;
0.3 kg of adenosine;
2.5 kg of sodium hexametaphosphate;
0.2 kg of ammonium sulfate;
0.3 kg of sodium chloride;
0.5 kg of magnesium chloride hexahydrate;
0.1 kg of manganese chloride monohydrate; and
0.5 kg of disodium hydrogen phosphate,
wherein the solution is uniformly stirred to prevent precipitation and the pH of the solution is adjusted to 7.0;
adding GshF enzyme 800 U/L, PPK enzyme 500 U/L, ADK enzyme 500 U/L, PAP enzyme 200 U/L and AK enzyme 600 U/L into the reaction system to start GSH production and to produce a reaction solution, wherein the added enzymes are crude enzyme liquid; and
controlling the pH of the reaction solution to 7.0 and the temperature of reaction system to 37° C. for a reaction period;
wherein, after reacting for 5 hours, the method further comprises measuring the amount of GSH produced by high performance liquid chromatography;
(2) separating the GshF enzyme by passing the reaction solution obtained in the step (1) through a filter by an ultrafiltration method to produce a filtrate and separated added enzymes, wherein the filtrate is the reaction solution without the added enzymes;
(3) isolating GSH and other materials from the filtrate obtained in step (3), wherein the step comprises:
adjusting the pH of the filtrate to 3.0 with hydrochloric acid;
passing the filtrate with a pH of 3.0 through an ion exchange column comprising D001 macroporous strongly acidic styrene cation exchange resin, wherein GSH is adsorbed and a through-liquid comprising ATP, ADP and AMP is produced;
collecting the through-liquid for ATP production or further purification of ATP, ADP and AMP; and
eluting GSH on the cation exchange resin with a 0-0.8M NaCl gradient;
(4) continuing GSH production in the reactor system, the step comprising:
adding the separated added enzymes produced in the step (2) into the reactor system through a return port of a filter;
adding new GshF enzyme, new PPK enzyme, new ADK enzyme, new PAP enzyme, and new AK enzyme at 5-10% of the original enzyme amount into the reactor system;
adding 100 L of the solution of step (1) into the reactor system; and
continuing GSH production with the reactor system maintained at 37° C. and pH of 7.0; and
(5) subjecting GSH isolated in step (3) to concentration, crystallization, and drying to produce a finished GSH.

* * * * *